United States Patent [19]

Watanabe

[11] Patent Number: 4,872,334

[45] Date of Patent: Oct. 10, 1989

[54] VARIABLE FLOW CAPILLARY GAS CHROMATOGRAPHY METHOD

[75] Inventor: Chuichi Watanabe, Niihashi, Japan

[73] Assignee: The Dow Chemical Company, Midland, Mich.

[21] Appl. No.: 287,692

[22] Filed: Dec. 20, 1988

Related U.S. Application Data

[63] Continuation of Ser. No. 47,801, May 8, 1987, abandoned.

[30] Foreign Application Priority Data

Sep. 5, 1986 [JP] Japan .................................. 61-104761

[51] Int. Cl.$^4$ .......................................... G01N 31/08
[52] U.S. Cl. ........................................ 73/23.1; 422/89
[58] Field of Search ........................... 73/23.1; 422/89; 436/161

[56] References Cited

U.S. PATENT DOCUMENTS

| | | | |
|---|---|---|---|
| 3,169,389 | 2/1965 | Green, Jr. et al. | 436/161 |
| 3,457,774 | 3/1967 | Clardy et al. | 73/23.1 |
| 3,607,075 | 9/1971 | Wolf | 422/89 |
| 4,045,998 | 9/1977 | Ford | 73/23.1 |
| 4,271,695 | 6/1981 | Sisti et al. | 73/23.1 |

FOREIGN PATENT DOCUMENTS

| | | | |
|---|---|---|---|
| 192863 | 11/1982 | Japan | 422/89 |
| 83052 | 5/1984 | Japan | 436/161 |
| 61-04761 | 5/1986 | Japan . | |

OTHER PUBLICATIONS

J&W Scientific, "High Resolution Chromatography Products", 1987/88, pp. 118-119.
Jennings et al., "Sample Injection in Gas Chromatography", J. of Chromatographic Science, vol. 24, Jan. 1986, pp. 34-40.
Lee et al., Open Tubular Column Gas Chromatography, Theory and Practice, ISBN 0-471-88024-8, (1984), pp. 116-118 and 166.
Lee et al., Open Tubular Column Gas Chromatography, Theory and Practive, ISBN 0-471-88024-8, (1984), pp. 195-198 and 227.
Nygren et al., "Applications of a Computerized Flow Programmer for Capillary Column Gas Chromatography", Anal. Chem., vol. 57, 1985, pp. 2748-2751.
Dodo et al., "Optimized Flow Programming for Temperature-Programmed Gas Chromatography", J. of Chromatography, 328 (1985), pp. 49-53.
Wicar, S., "Mass Flow Control and Temperature Programming in Gas Chromatography", J. of Chromatography, 295, (1984), pp. 395-403.
Nohl, A., "Flow Programming of Short Capillary Columns", Chromatography Review, vol. 11, No. 3, Oct. 1984.
Nygren et al., "Flow Programming in Glass Capillary Column-Electron Capture Gas Chromatography by Using the Valve in the Splitter Line", J. of Chromatography, 123, (1976), pp. 101-108.

Primary Examiner—Hezron E. Williams
Attorney, Agent, or Firm—Timothy S. Stevens

[57] ABSTRACT

A method for temperature programmed capillary column gas chromatography characterized in that carrier gas is flowed in an amount greater than that under normal separation conditions for a term starting from before injection of a sample or immediately after the injection and ending at any time point from immediately after a solvent in the sample commences to enter into a column to the solvent finishing passing through the column. The invention is also apparatus for the above method characterized in that the apparatus has two flow paths for carrier gas which, for example, join to one flow path before a sample injection device, and one of the flow paths has a valve which can rapidly stop or decrease the flow of the carrier gas in that flow path.

7 Claims, 1 Drawing Sheet

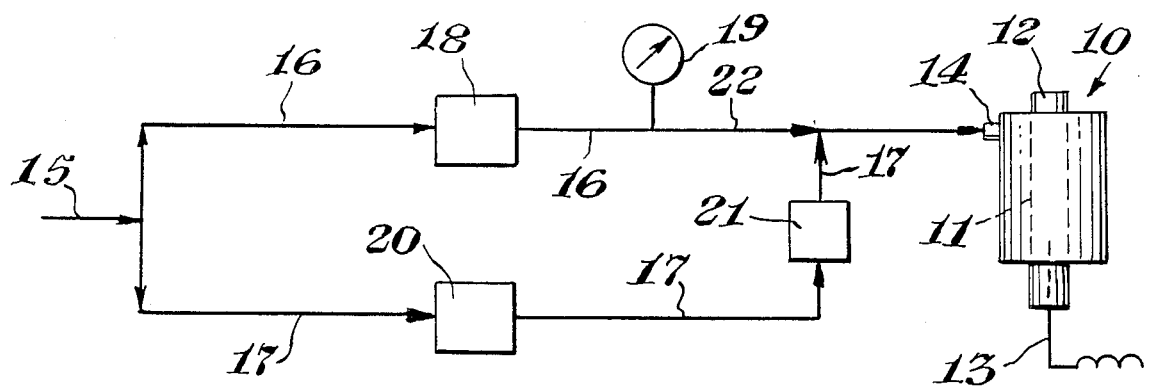
Fig. 1
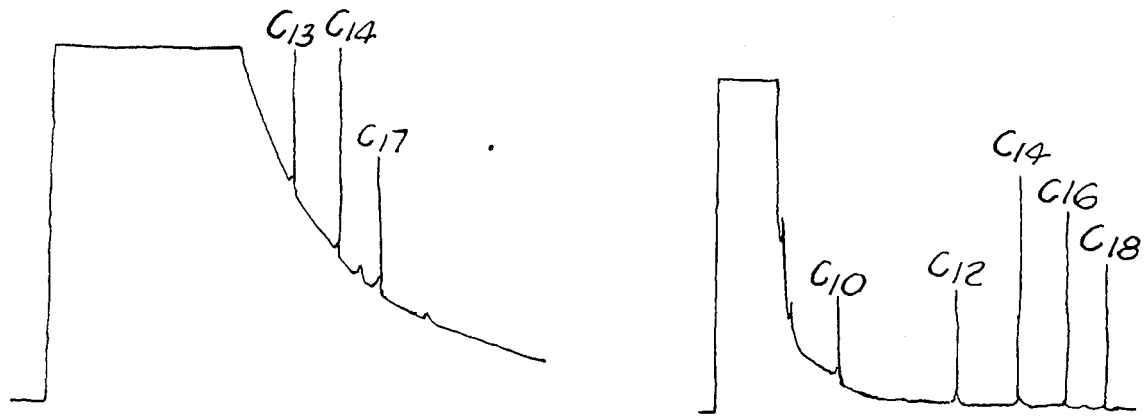
Fig. 2
Fig. 3
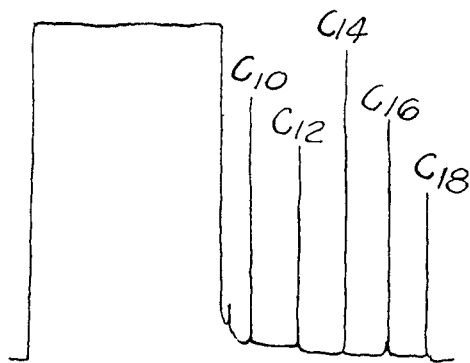
Fig. 4

VARIABLE FLOW CAPILLARY GAS CHROMATOGRAPHY METHOD

This is a continuation of application Ser. No. 047,801, filed May 8, 1987, now abandoned.

FIELD OF THE INVENTION

The invention is in the field of gas chromatography and more specifically in the field of capillary column gas chromatography.

BACKGROUND OF THE INVENTION

Capillary column gas chromatography (CC-GC) is an important branch of chemical analysis. CC-GC is widely used as a sensitive technique for the analysis of trace components because using this technique it is possible to resolve a multiplicity of components contained in a sample in trace quantities. A wide variety of CC-GC methods and apparatuses have been developed.

A relatively large volume of the sample has to be injected to detect and determine components present in the sample at extremely low concentrations. However, with CC-GC the sample capacity is so limited that when a relatively large volume of the sample is injected into the injection port, detection of the components subject to analysis frequently becomes difficult or their determination becomes inaccurate because of the severe tailing of the solvent of the sample, which causes the peaks of the components of interest with relatively short retention times to overlap with those of the tailing solvent. This is caused by a part of the large quantity of the solvent in the sample flowing slowly into the capillary column over a considerable period of time after inflow of the components subject to analysis has taken place, in spite of the fact that ideally the vapors of the solvent and all the components of interest should flow into the column at about the same time.

The injection modes for capillary gas chromatography can be divided broadly into four categories; (1) the split mode; (2) the splitless mode, (3) the on-column mode and (4) the direct mode, as discussed in detail in the article "Sample Injection In Gas Chromatography" by Walter Jennings et al in Journal of Chromatographic Science, Vol. 24, January 1986, pp 34-40, which is herein fully incorporated by reference.

In the split mode generally a small volume of liquid sample, comprising a low boiling solvent and the sample components of interest, is flash vaporized in a chamber having a carrier gas flowing therethrough. The flow of vaporized sample in the carrier gas is then split so that, for example, about 99% of the flow is discarded and only about 1% enters the column. The split mode can provide good separation between the solvent and the sample components of interest, i.e.. little solvent "tailing", but at the expense of sensitivity of detection of the sample components of interest. It has long been needed in capillary gas chromatography to develop an injection mode having little solvent tailing and improved sensitivity.

In the splitless mode of injection, a relatively dilute sample is vaporized slowly (e.g., 30 seconds) into the column and then, after a suitable delay, the injection port is purged to prevent tailing by the solvent of the sample. Pre-concentration of the sample can be required for trace analysis because the maximum injectable amount of the sample is 1-2 microliters in this mode of injection. The splitless mode can provide good separation between the solvent and the sample components of interest, i.e., little solvent tailing, but as the expense of operational ruggedness, e.g., small differences in the way the sample is injected by a syringe can have profound qualitative and quantitative effects as discussed by Jennings et al, and a portion of the analytical components of interest can be lost due to the purging of the injection port. It has long been needed in capillary gas chromatography to develop an injection mode having little solvent tailing and a high degree of operational ruggedness.

In the on-column injection mode the sample is injected into the column. However, this mode of injection is generally thought to be limited to the injection of relatively small volumes of sample and other problems as discussed by Jennings et al which limitation also limits the sensitivity of detection of the sample components of interest.

In the direct injection mode, the sample is injected into a heated chamber and vaporized. The vaporized sample is then flowed into the column by the carrier gas without splitting. Capillary columns having internal diameters of more than 0.5 millimeter are less sensitive to injection problems and have been adapted to injectors designed for use with packed columns as shown by Jennings et al in FIG. 6 and in FIG. 7. The adaptions shown include the provision of a cylinder inserted into a packed column injector. The sample is vaporized in the cylinder and then entirely introduced into the column without splitting. This general approach has also been applied to conventional capillary columns having an internal diameter of less than 0.5 millimeter, where injection problems can be severe, as described in a book by Milton L. Lee et al entitled "Open Tubular Column Gas Chromatography" 1984, published by John Wiley & Sons, ISBN 0-471-88024-8, pp 116-118, herein fully incorporated by reference. Lee et al describe a sample vaporization cylinder of 0.7 millimeter internal diameter and states that "The goal of having minimum injector contribution to bandspreading can be achieved by using a narrow-bore vaporization chamber." The direct injection system described by Lee et al requires a slow injection of a sample volume greater than about 1 microliter to prevent undesirable backflushing of vaporized sample down the septum purge incorporated therein. Thus, the direct injection method for the injection of a relatively large volume of sample has been applicable only to capillary columns having an internal diameter of more than 0.5 millimeter to obtain good separations of the peak of the solvent and those of the substances subject to analysis in the sample, and it is virtually inapplicable to capillary columns of smaller inside diameter because of severe tailing.

It is, therefore, an object of the present invention to provide a chromatographic analytical apparatus and method most preferably applicable for permitting a relatively large sample injection volume onto a capillary column of relatively small internal diameter so that the components of interest in the sample may be sensitively detected, and with a significant reduction in the aforementioned problem of solvent tailing.

SUMMARY OF THE INVENTION

The invention is an apparatus for temperature programmed capillary column gas chromatography comprising: (a) a sample injection port; (b) a capillary gas chromatography column, the inlet of which is in fluid communication with the sample injection port; (c) a first means for continuously flowing carrier gas into the sample injection port, such as a system comprising a pressure regulation type gas chromatography flow controller; and (d) a second means for flowing additional carrier gas into the sample injection port comprising a flow control valve which can rapidly stop or decrease the flow of additional carrier gas into the sample injection port, such as a system comprising a mass flow controller and an electrically operated on-off valve.

The invention is also a method for temperature programmed capillary column gas chromatography comprising five steps. The first step is to flow a carrier gas through a gas chromatography injection port with essentially all of the carrier gas subsequently flowing into a gas chromatography capillary column at a first flow rate and a first pressure. The second step is to heat the column to a first temperature in, for example, a conventional column oven. The third step is to introduce a sample through the injection port with, for example, a microsyringe. The sample comprises a solvent and a component of interest in the analysis. The fourth step is to reduce the flow rate of the carrier gas to a second flow rate at a time longer than immediately after beginning the step of introducing the sample. The second flow rate being a normal flow rate for the column, i.e., a flow rate normally used for chromatography on the column. The last step is to increase the temperature of the column so that the component of interest emerges from the column, i.e., to perform temperature programmed gas chromatography including detecting the component of interest after it emerges from the column. The method of the invention can further comprise the step of heating the injection port and the carrier gas therein to a temperature effective to vaporize a sample injected thereinto, i.e., direct injection. Alternatively, the sample can be introduced through the injection port directly into the inlet of the column, i.e., on-column injection.

BRIEF DESCRIPTION OF THE DRAWINGS

FIG. 1 is a schematic view of the apparatus embodiment of the invention.

FIG. 2 is a reproduction of the chromatogram of the Comparative Example.

FIG. 3 is a reproduction of the chromatogram of Example 1.

FIG. 4 is a reproduction of the chromatogram of Example 2.

DETAILED DESCRIPTION OF THE INVENTION

In the method embodiment of the present invention, the aforementioned problem of solvent tailing is minimized and, therefore, favorable separations of the peaks of the components having short retention time from the peak of the solvent are obtained because of the greater flow of the carrier gas during the initial time intervals of the method. The initially greater flow of carrier gas results in the solvent, which is vaporized either in the injection port or in the column, flowing out of the column in a relatively short period of time. Furthermore, the following reduced flow rate of the carrier gas is more optimum for the chromatographic separation of the component of interest of the sample. The initially high flow rate of carrier gas does not adversely affect this separation in most cases.

The second flow rate of carrier gas, e.g., helium gas, can vary according to various factors such as the inside diameter of the capillary column, the column temperature program and type of substance subject to analysis, and is determined by the experience of the analyst and preliminary experiments as is well known in the art. For example, the flow rate in the case of a column with an inside diameter of about 0.2 millimeter is often in the range of about 0.5 to 1.5 milliliters per minute, and in the case of a column with an inside diameter of about 0.3 millimeter is often in the range of about 1 to 3 milliliters per minute.

On the other hand, the first flow rate of the carrier gas is greater than that under usual separation conditions. The extent to which the first flow rate is increased varies with the amount of the sample injected, type of the solvent in the sample, and the difference between the retention time of the solvent and the component of interest of the sample, making it difficult to specify the exact increment. In order to reap the full advantage of the present invention, however, it is preferable that the first flow rate be more than about 1.5 times the second flow rate. Increasing the first flow rate to a considerable extent over this value has little adverse effect on the results of the analysis, and it is therefore often desirable that the first flow rate be as large as possible for the prevention of solvent tailing. However, it is necessary to increase the pressure of the carrier gas fed into the sample injection port to increase the flow rate of the carrier gas, but the excessive pressure may give rise to the leakage of the gas from various joints and may give rise to difficulty in injection by a microsyringe which in turn leads to problems such as variations in the analytical results. Therefore, the first pressure of the carrier gas is preferably less than about 10 killograms per square centimeter.

In the method of the present invention, either the sample may be injected while charging the carrier gas in the above-mentioned high flow range or the flow rate of the carrier gas may be switched to a high flow rate immediately after sample injection. The aforementioned high flow rate of the carrier gas may be reduced to the second flow rate at any arbitrary time immediately after beginning the sample injection. Preferably, the time for the reduction in carrier gas flow rate is no longer than after the vaporized solvent in the sample has passed through the column as evidenced by observing the chromatogram of the solvent peak, i.e., by seeing the solvent peak begin to approach the baseline again, and preferably no shorter than 3 seconds after beginning the sample injection. Maintaining the first flow rate beyond the time when essentially all of the solvent has emerged from the column can be done but may sometimes adversely affect the analytical results. The sample can be injected into a heated direct injection type sample injection port, wherein the sample is vaporized, and in this event it is preferable that the rate of injection be relatively slow, e.g., 2.5 microliters per second to best reduce solvent tailing. Alternatively, the sample can be injected through the sample injection port directly into the inlet of the column, and in this event it is also preferable to inject slowly. The inlet of the column can be active, i.e., coated with a chromatographically active stationary phase, or can be a length of uncoated deactivated capillary tubing conventionally known as a "retention gap."

The method of the present invention is preferably carried out under temperature program conditions for the column as is well understood in the art. In this case, the first temperature of the column is preferably set to within 10 degrees centrigrade of the atmospheric pressure boiling point of the solvent of the sample and the rate of increasing the temperature of the column is determined by the separation conditions for the component of interest of the sample. Unless the method is carried out under the temperature programmed conditions, the retention time of the component of interest will be undesirably prolonged when the first temperature of the column is set as described above and a relatively low boiling point solvent is used.

Referring to FIG. 1, therein is shown a schematic view of a typical apparatus for carrying out the above-mentioned method including a sample injection port 10 of the direct injection type. The port 10 comprises a heated sample vaporization chamber 11 and a septum 12. A capillary column 13 is connected to the port 10. The capillary column 10 can include an initial portion that is not coated with a chromatographically active phase, i.e., the inlet of the column can be a "retention gap" as described in Example 1 below. Preferably, the capillary column 13 has an internal diameter of less than about 0.5 millimeter since as previously mentioned, the problem of solvent tailing is more severe with such columns. A flow of carrier gas 15 is split into a stream 16 and a stream 17. The stream 16 is directed through a flow controller 18. Preferably, the flow controller 18 is a conventional capillary column flow controller of the pressure regulation type. A pressure gauge 19 is provided to measure the carrier gas pressure. The stream 17 is directed through a flow controller 20 and a flow control valve 21 and then joins the stream 16 to form a combined stream 22 which enters an inlet 14 of the injection port 10. Preferably, the flow controller 20 is a mass flow controller and the valve 21 is an electrically operated on-off valve. The flow controller 18 is used to control the flow of carrier gas continuously into the sample injection port 10. The flow controller 20 is set so that when the valve 21 is open, the flow rate of the stream 17 is at least 1.5 times greater than the flow rate of the stream 16. When the valve 21 is closed the flow rate of the stream 22 decreases to essentially the same flow rate as the stream 16.

Comparative Example

A normally operating Hewlett Packard Model 5890A gas chromatograph having a packed column injection port and an associated strip chart recorder to record chromatograms therefrom is fitted with a 2 millimeter internal diameter glass inlet liner in the injection port. The inlet liner extends into the oven of the chromatograph only far enough to allow its connection to a 10 meter long fused silica retention gap, 0.32 millimeter internal diameter, uncoated and deactivated with diphenyl tetramethyl disilizane (DPTMDS). The other end of the retention gap is connected to a 25 meter long fused silica Quadrax brand (New Haven, CT) capillary column, 0.32 millimeter internal diameter, methylsilicone stationary phase having a film thickness of 0.17 micrometer., The outlet of the column is connected to the detector of the chromatograph. The column oven temperature program is 70° C. for 2 minutes after injection and then a rise of 20° C. per minute to 250° C. The injection port temperature is 250° C. The carrier gas flow rate is 2.3 milliliters of helium per minute. A standard of 2 parts per million each of C9, C11, C13, C15, and C17 hydrocarbons in hexane solvent is prepared. A 20 microliter injection of the standard is made into the injection port. A chromatrgram results from the injection and this chromatogram is reproduced in FIG. 2.

The chromatogram reproduced in FIG. 2. shows severe solvent tailing. The solvent tailing is so bad that the C9 and C11 peaks are swamped by the solvent tailing and not apparent in the chromatogram.

EXAMPLE 1

The chromatographic system of the Comparative Example is modified as generally shown in FIG. 1. The mass flow controller 20 is a Porter Instrument Company (Hatfield, PA) Model 201-SSVB mass flow controller set to deliver 5 milliliters of helium per minute. The valve 21 is a Cheminert solenoid valve (catalog No. H2001, the Anspec Co., Ann Arbor, MI). When the solenoid valve is on, the total carrier flow rate into the injection port is 2.3 milliliters per minute. The column oven temperature program is 70° C. for 3 minutes after injection and then a rise of 20° C. per minute to 250° C. The injection port temperature is 250° C. The solenoid valve is turned on when an injection is made and is turned off 1.8 minutes later. A standard of 2 parts per million each of C10, C12, C14, C16, and C18 hydrocarbons in hexane solvent is prepared. A 20 microliter injection of the standard is made into the injection port. A chromatogram results from the injection and this chromatogram is reproduced in FIG. 3.

The chromatogram reproduced in FIG. 3. shows much less solvent tailing than the chromatogram reproduced in FIG. 2. The solvent tailing in FIG. 3 is so well controlled that even the C10 peak is apparent.

This example shows the advantage of the present inventive method and apparatus relative to a prior approach as shown in the Comparative Example.

EXAMPLE 2

The same system and conditions are used in this example as are used in Example 1. A 100 microliter injection of the standard is made into the injection port. A chromatogram results from the injection and this chromatogram is reproduced in FIG. 4.

The chromatogram reproduced in FIG. 4. shows much less solvent tailing than the chromatogram reproduced in FIG. 2 despite the fact that the injection volume is 5 times greater.

EXAMPLE 3

A J&W Scientific (Folsom, CA) On-Column Injector (U.S. Pat. No. 4,440,550) is mounted on a Hewlett Packard 5880 gas chromatograph (GC) having an associated integrator/recorder to record the chromatograms therefrom. A capillary column is assembled and includes a retention gap consisting of a 20 meter long section of 0.53 millimeter internal diameter fused silica deactivated with DPTMDS supra, connected to a J&W 30 meter long, 0.32 millimeter internal diameter fused silica column coated with a 1 micron thick film of DB-5. This column is mounted in the GC with the retention gap end connected to the injector and the other end of the assembly connected to the detector. The column oven temperature program is 70° C. for 8 minutes after injection begins and then a rise of 10° C. per minute to 220° C. The Flame Ionization Detector is set at 250° C. The first flow rate of carrier (hydrogen) is 30 milliliters per minute. The second flow rate of carrier is 8 milliliters per minute. A standard is prepared containing about 200 parts per billion each of ethyl benzene, phenol, octanol, nonenol, trichloro benzene, trichloro phenol, C-14 hydrocarbon, C-15 hydrocarbon and C-16 hydrocarbon in hexane. A 200 microliter on-column injection of the standard is made at a rate of about 1.1 microliters per second, i.e., a 3 minute injection, and 8 minutes after beginning the injection the flow rate of carrier gas is reduced. The solvent peak is essentially back to baseline at about 8 minutes, well before the ethyl benzene peak is seen at 10 minutes. The phenol peak is seen at 11.2 minutes, the octanol peak at 12.6 minutes, the nonenol peak at 14 minutes, the trichloro benzene peak at 14.2 minutes, the trichloro phenol peak at 16.7 minutes, the C-14 peak at 17.3 minutes, the C-15 peak at 18.6 minutes and the C-16 peak at 19.8 minutes.

What is claimed is:

1. A method for temperature programmed capillary column gas chromatography, comprising the steps of:
   flowing a carrier gas through a gas chromatography injection port with essentially all of the carrier gas subsequently flowing into a gas chromatography capillary column at a first flow rate and a first pressure;
   heating the column to a first temperature;
   introducing a sample through the injection port, the sample comprising a solvent and a component of interest;
   reducing the flow rate of the carrier gas to a second flow rate at a time longer than immediately after beginning the step of introducing the sample, the second flow rate being a normal flow rate for the column; and
   increasing the temperature of the column so that the component of interest emerges from the column.

2. The method of claim 1 wherein the first flow rate is more than about 1.5 times higher than the second flow rate.

3. The method of claim 1 wherein the first pressure is less than about 10 kilograms per square centimeter.

4. The method of claim 1 wherein the first temperature of the column is within 10 degrees centigrade of the atmospheric pressure boiling point of the solvent of the sample.

5. The method of claim 1 further comprising the step of heating the injection port and the carrier gas therein to a temperature effective to vaporize a sample injected thereinto.

6. The method of claim 1 wherein the step of introducing a sample through the injection port consists essentially of introducing the sample through the injection port directly into the inlet of the column.

7. The method of claim 1 wherein the flow rate of the carrier gas is reduced at a time longer than 3 seconds after beginning the step of introducing the sample and shorter than the time after essentially all of the solvent has emerged from the column.

* * * * *

UNITED STATES PATENT AND TRADEMARK OFFICE
CERTIFICATE OF CORRECTION

PATENT NO. : 4,872,334

DATED : Oct. 10, 1989

INVENTOR(S) : Chuichi Watanabe

It is certified that error appears in the above-identified patent and that said Letters Patent is hereby corrected as shown below:

Cover page, under "OTHER PUBLICATIONS", fourth item, delete "Practive" and insert --Practice--.

Col. 2, line 2, delete "as" and insert --at--.

Col. 5, line 1, delete "centrigrade" and insert --centigrade--.

Col. 6, line 15, delete "2.3" and insert --7.3--;
    line 15, after the sentence ending with "minute.", insert the following sentence --When the solenoid valve is off, the carrier flow rate into the injection port is 2.3 milliliters per minute.--.

Signed and Sealed this

Thirtieth Day of October, 1990

*Attest:*

HARRY F. MANBECK, JR.

*Attesting Officer*  *Commissioner of Patents and Trademarks*